United States Patent [19]

Hintermaier et al.

[11] Patent Number: 5,463,055

[45] Date of Patent: Oct. 31, 1995

[54] PROCESS FOR THE PRODUCTION OF 2-ETHOXY-4,6-DIHYDROXYPYRIMIDINE OR ITS ALKALI SALTS

[75] Inventors: Helmut Hintermaier, Trostberg; Ursula Maier, Tacherting; Stefan Weiss, Trostberg, all of Germany

[73] Assignee: SKW Trostberg Aktiengesellschaft, Trostberg, Germany

[21] Appl. No.: 172,494

[22] Filed: Dec. 22, 1993

[30] Foreign Application Priority Data

Dec. 24, 1992 [DE] Germany .......................... 42 44 132.3
Sep. 15, 1993 [DE] Germany .......................... 43 31 223.3

[51] Int. Cl.$^6$ ........................................... C07D 239/02
[52] U.S. Cl. ................................................ 544/299
[58] Field of Search ...................................... 544/299

[56] References Cited

U.S. PATENT DOCUMENTS 3,322,526  5/1967  Loux ........................ 544/299
4,059,696  11/1977  Maurer et al. ................. 424/200
5,250,689  10/1993  Roduit et al. .................. 544/299
5,266,697  11/1993  Escher et al. .................. 544/299

FOREIGN PATENT DOCUMENTS 2523324  12/1976  Germany .

*Primary Examiner*—Cecilia Tsang
*Attorney, Agent, or Firm*—Felfe & Lynch

[57] ABSTRACT

A process is described for the production of 2-ethoxy-4,6-dihydroxypyrimidine or its alkali salt which is an important intermediate in the field of pharmaceuticals and agrochemicals. This compound can be produced using the process according to the invention in good yields and high purity by reacting an O-ethylisourea salt that is preferably formed as an intermediate from cyanamide or chloroformamidinium salts or free O-ethylisourea with an alcoholate and a malonic acid dialkyl ester or a salt of the malonic acid dialkyl ester in alcohol and, if desired, subsequent acidification.

28 Claims, No Drawings

PROCESS FOR THE PRODUCTION OF 2-ETHOXY-4,6-DIHYDROXYPYRIMIDINE OR ITS ALKALI SALTS

The present invention concerns a process for the production of 2-ethoxy-4,6-dihydroxypyrimidine (or tautomeric forms thereof) or its alkali salts.

Pyrimidine derivatives have numerous uses as intermediates and final products particularly in the field of pharmaceuticals and agrochemicals. Thus their use in fungicides or herbicides is well known. Substituted alkoxy pyrimidines are also of interest as intermediates in this connection.

The synthesis of 4,6-dihydroxy-2-methoxypyrimidine was achieved by S. Basterfield and E. C. Powell (Canad. J. Res. 1 265 f (1929)) by reacting malonic acid dimethyl ester with O-methylisourea and by H. Bretschneider, J. Dehler and W. Klötzer (Mh. Chem. 95, 207 (1964)) from the hydrochloride of O-methylisourea by reaction with malonic acid dimethyl ester in the presence of sodium methylate. C. J. Moye (Aust. J. Chem..17, 1309 f (1964)) obtained 4,6-dihydroxy-2-methoxypyrimidine by reacting O-methylisourea monomethylsulfate with malonic acid diethyl ester and sodium methylate.

However, transfer of the laboratory syntheses of 4,6-dihydroxy-2-methoxypyrimidine known from the literature to the production of analogous 2-ethoxy compounds on a technical scale causes the following problems:

In analogy to the process of Bretschneider and co-workers, the production of 2-ethoxy-4,6-dihydroxypyrimidine requires O-ethylisourea hydrochloride which is very difficult to produce economically and on a technical scale.

Due to the good solubility of O-ethylisourea hydrochloride in ethanol the yields obtained are not good;

due to the strong corroding powder of O-ethylisourea hydrochloride a very expensive special equipment is necessary for its isolation and drying;

solid O-ethylisourea chloride readily cleaves off ethyl chloride.

Whereas O-methylisourea salts have a broad use for the synthesis of heterocycles, syntheses of heterocyclic 5 and 6 rings by reacting $C_3$ building blocks with O-ethylisourea salts in the presence of a sodium alcoholate are not known. In heterocycle syntheses O-ethylisourea is less reactive towards $C_3$ building blocks than O-methylisourea which is due to steric reasons.

From the state of the art it has to be expected that the synthesis of 2-ethoxy-4,6-dihydroxypyrimidine or its alkali salt according to the known production processes by reaction of a malonic acid ester with an O-ethylisourea salt in the presence of sodium alcoholate is not possible on a technical scale in an economic manner. This assumption is confirmed by the fact that there are no details about the production process, the yield obtained and the purity of the product in the German patent disclosure DE 25 23 324 and in the Belgian patent specification BE 833 082 in which 2-ethoxy-4,6-dihydroxypyrimidine is mentioned. Furthermore the compound is neither characterized by an elemental analysis nor by details of the melting point or a spectrum.

It was therefore the object to provide a process which can be used to synthesize 2-ethoxy-4,6-dihydroxypyrimidine or its alkali salts without the aforementioned problems on a technical scale under economic conditions and with as small amounts as possible of by-products and residual substances.

It surprisingly turned out that 2-ethoxy-4,6-dihydroxypyrimidine or salts thereof can be produced on a technical scale in an economic manner with a very high purity, good yields and a favourable ecological balance with the aid of the present invention.

The present invention concerns a process for the production of 2-ethoxy-4,6-dihydroxypyrimidine or its salts. According to the invention O-ethylurea or a salt thereof is reacted for this with a malonic acid dialkyl ester or an alcoholate or a salt of the malonic acid dialkyl ester in the presence of a solvent at −10° to 180° C. and, if desired, the salt of the 2-ethoxy-4,6-dihydroxypyrimidine obtained is converted by an acid into the free pyrimidine derivative.

In a preferred embodiment of the process according to the invention 2-ethoxy-4,6-dihydroxypyrimidine or its salts are prepared using three or two consecutive reaction steps. For this O-ethylisourea or a salt thereof is produced from cyanamide or chloroformamidinium salts in process step (a).

In the second process step (b) the O-ethylisourea or its salt which was formed is reacted with a malonic acid dialkyl ester and an alcoholate or with a salt of the malonic acid dialkyl ester to form the salt of the 2-ethoxy-4,6-dihydroxypyrimidine.

The third process step (c) comprises, if desired, releasing 2-ethoxy-4,6-dihydroxypyrimidine from the salt of 2-ethoxy-4,6-dihydroxypyrimidine or its tautomeric forms by addition of an acid.

According to the invention isourea or a salt thereof can also be produced in situ i.e. in a preferred embodiment isourea or its salts are produced as intermediates and reacted without further purification.

The production of the O-ethylisourea salt can be achieved according to the invention by reacting cyanamide with ethanol in the presence of a mineral acid or anhydrous hydrogen chloride or a strong organic acid.

This reaction is preferably carried out in the temperature range −10° to +90° C. Concentrated sulfuric acid (>95%) is for example used as the mineral acid. A further preferred variant of the process utilizes a mixture of technical sulfuric acid and fuming sulfuric acid as the mineral acid. However, fuming sulfuric acid itself is also suitable for the said reaction. The amount of $SO_3$ in the sulfuric acid should in any case be such that the amount of water that is introduced by the other reaction partners such as ethanol is converted completely to sulfuric acid.

Acids with a $pK_a$ of $\leq 3$ come into consideration as strong organic acids. Sulfonic acids such as methane-sulfonic acid, benzenesulfonic acid and p-toluene-sulfonic acid or haloacetic acids such as trichloroacetic acid are preferably used.

1 to 2 val mineral acid, preferably 1 to 1.2 val mineral acid, or 1 to 2 mole hydrogen chloride, preferably 1 to 1.2 mole hydrogen chloride are used per 1 mole cyanamide. Ethanol is usually used in excess, the excess ethanol serving as a solvent. The ratio of cyanamide to ethanol can be varied within wide limits. The minimum amount of ethanol must, however, be such that on a technical scale the reaction mixture is still present in a state which can be stirred and pumped. In general 2.5 to 6.5 mole ethanol is used per 1 mole cyanamide. The reaction temperature depends on the strength of the acid. The reaction is preferably carried out in the temperature range −10° to +50° C., in particular at 5° to 30° C.

According to the invention O-ethylisourea hydrochloride can surprisingly also be produced by reaction of cyanamide with ethanol in the presence of a compound that cleaves off hydrogen chloride such as e.g. silicon tetrachloride or thionyl chloride. The use of a compound that cleaves off HCl has the advantage that it is not necessary to work with corrosive hydrogen chloride. The reaction is preferably carried out at temperatures in the range −10° to +90° C., reaction temperatures of −5° to +40° C. being particularly advantageous.

The compound that cleaves off HCl is usually used in such an amount that ca. 1 mole cyanamide is used per mole released chlorine. Thus for example the mole ratio of cyanamide:silicon tetrachloride is 1:0.25, larger excesses are, however, not critical.

In addition to the said possibilities of synthesis using cyanamide as the starting compound, chloroformamidinium salts are also suitable according to the invention for producing the isourea salt: for this chloroformamidinium chloride is for example reacted with ethanol, whereby it is also possible to carry out this reaction according to the present invention in the presence of cyanamide. The mole ratio of chloroformamidinium chloride to cyanamide is about 1:1. Ethanol is used in excess. The reaction preferably takes place in a temperature range of 10° to 90° C. Other salts such as e.g. the nitrate can also be used instead of chloroformamidinium chloride.

The major technical and economic advantage of the present invention is among others that the O-ethylisourea salt does not have to be isolated and dried. The O-ethylisourea salt produced in situ can be reacted directly without prior isolation in the second reaction step. The O-ethylisourea salt can be used in the form of a solution or suspension preferably in ethanol. In addition the O-ethylisourea base can be released directly from the salt by addition of alcoholate and in particular alkali alcoholate.

According to the state of the art it would not have been expected that O-ethylisourea salts produced in situ could be reacted without isolation and purification in the presence of all impurities to form pure 2-ethoxy-4,6-dihydroxypyrimidine. Previous experience has shown that syntheses of heterocycles are very sensitive to impurities in the starting materials. Of course the O-ethylisourea salts can also be used in the form of pure isolated substances.

In process step (b) O-ethylisourea or its salt is subsequently reacted with a malonic acid dialkyl ester in the presence of an alcoholate at temperatures between −10° and 180° C., preferably between 70° and 140° C. The reaction takes place in the presence of a solvent or/and excess malonic acid dialkyl ester. An alcohol such as e.g. ethanol or a mixture of ethanol and methanol is preferably used as the solvent, however, it is also possible to use other solvents such as e.g. hydrocarbons or ether. If the O-ethylisourea salt is used as an ethanolic solution or suspension and the alcoholate is used as an alcoholic solution then it is not usually necessary to add a further amount of solvent. Alkali alcoholates, in particular sodium and potassium alcoholates of aliphatic primary, secondary or tertiary alcohols in a solid form or as alcoholic solutions are preferably used as alcoholates. Sodium ethylate is preferably used for the production of very pure 2-ethoxy-4,6-dihydroxypyrimidine. 2-Methoxy-4,6-dihydroxy-pyrimidine is formed as a byproduct in the presence of sodium methylate and methanol. The use of cheap technical 30% methanolic sodium methylate solution is therefore of particular interest when a high purity of the product is not important.

Aliphatic malonic acid esters in particular with 1 to 4 carbon atoms and preferably malonic acid diethyl esters are used as the malonic acid dialkyl esters. The malonic acid dialkyl ester can be used in stoichiometric amounts up to a large excess. 1 to 1.5 mole malonic acid dialkyl ester are preferably used per 1 mole cyanamide or per 1 mole O-ethylisourea cation or per 1 mole O-ethylisourea base. The malonic acid dialkyl ester can, however, also be used as the solvent.

Instead of the malonic acid dialkyl ester it is also possible according to the invention to use its salts and in particular alkali salts such as the sodium or potassium salt. Alkali salts of malonic acid dialkyl ester can be prepared in a simple manner by for example reacting malonic acid dialkyl ester with an alkali alcoholate such as sodium ethylate or methylate. The alkali salts of the malonic acid dialkyl ester can be produced in situ. In this case an O-ethylisourea salt is preferably reacted in process step (b) with a sodium malonic acid dialkyl ester, in particular with sodium malonic acid diethyl ester. In this variant the sodium malonic acid dialkyl ester functions as a strong base as well as the source of malonic acid dialkyl ester.

The O-ethylisourea base can be used as a pure isolated substance. However, surprisingly it was also found that the present invention also enables the use of crude impure O-ethylisourea produced in situ. The non-isolated O-ethylisourea formed as an intermediate is used as a solution in ethanol or in a mixture of ethanol and methanol.

In a preferred embodiment of the process according to the invention the mole ratio of isourea or its salt to the alcoholate or to the salt of the malonic acid dialkyl ester is 1:1 to 8. When using an O-ethylisourea salt of a monovalent acid 1 to 4 mole alcoholate and preferably 2 to 2.5 mole alcoholate are usually used per 1 mole O-ethylisourea salt. When using an O-ethylisourea salt of a divalent acid, 2 to 8 mole alcoholate and preferably 4 to 5 mole alcoholate are generally used per 1 mole O-ethylisourea salt. When using O-ethylisourea hydrogen sulfate 2 to 5 mole alcoholate and preferably 3 to 4.5 mole alcoholate are generally used per 1 mole O-ethylisourea salt. When using an O-ethylisourea base the presence of an alcoholate is not absolutely necessary, however, 1 to 1.5 mole alcoholate are preferably used per 1 mole O-ethylisourea to achieve an optimal yield.

According to the present invention process step (b) can be carried out as follows: pure crystalline O-ethylisourea salt or non-isolated O-ethylisourea salt produced in situ or free O-ethylisourea is admixed as an ethanolic solution or suspension with an alcoholate, preferably sodium ethylate, as a solid substance or alcoholic solution. Subsequently the malonic acid dialkyl ester is added. In order to complete the reaction it is restirred.

However, the malonic acid dialkyl ester and the O-ethylisourea salt in the form of an ethanolic solution or suspension or the free O-ethylisourea can also be added first. In the case of the O-ethylisourea salt it may be a product produced as an intermediate or a pure substance. Alcoholate is subsequently added as a solid product or as an alcoholic solution preferably at −10° to 150° C. The reaction is completed by restirring.

According to a further embodiment the procedure comprises adding the malonic acid dialkyl ester as a solvent and then adding an alcoholic reaction mixture of O-ethylisourea salt and alkali alcoholate at 80° to 180° C. Instead of the reaction mixture of O-ethylisourea salt and alcoholate, it is also possible according to the invention to use an alcoholic mixture of O-ethylisourea and alcoholate, or alternatively the O-ethylisourea salt or O-ethylisourea and the alcoholate are added separately to the malonic acid dialkyl ester which is added first.

It was surprisingly found that 2-ethoxy-4,6-dihydroxypyrimidine can even be produced at high temperatures without substantially reducing the purity and yield. This would not have been expected according to the state of the art according to which O-ethylisourea is not a very stable compound since O-ethylisourea has a strong tendency to decompose or trimerize.

According to the state of the art it would not have been expected that process step (b) would allow the production of 2-ethoxy-4,6-dihydroxypyrimidine or its salt under technically feasible, economical and ecological conditions.

In process step (c) the salt of 2-ethoxy-4,6-dihydroxypyrimidine (in particular the sodium or potassium salt) obtained in process step (b) can then be converted by an acid into the desired 2-ethoxy-4,6-dihydroxypyrimidine. For this the reaction mixture is concentrated following process step (c) to the extent that a mixture which still can be stirred is present. After addition of water, the pH value is adjusted to 2.0 to 9.0 preferably to 3.5 to 5.5. The procedure can also be that water is added during the removal of the alcohol or the solvent by distillation.

In a further embodiment the pyrimidine salt, if desired, together with the alkali salt of the acid which is used, is isolated in a solid form. This can be carried out by filtration in which case the reaction mixture must if necessary be previously concentrated by evaporation or it can be carried out by evaporating the reaction mixture to dryness in a dryer or thin layer evaporator. The isolated pyrimidine salt is dissolved or suspended in water and subsequently acidified. The acidification is carried out with a mineral acid or a carboxylic acid e.g. acetic acid. 2-Ethoxy-4,6-dihydroxypyrimidine is formed in a crystalline form.

The 2-ethoxy-4,6-dihydroxypyrimidine which is formed in this manner as a solid substance is washed free of salt using water in a subsequent processing step if desired and subsequently dried if desired.

The process according to the invention allows the synthesis of 2-ethoxy-4,6-dihydroxypyrimidine without the isolation of products formed as intermediates in good yields and high purity.

It is intended to further elucidate the invention in the following examples.

EXAMPLES

Example 1

Starting compounds

Cyanamide and hydrogen chloride in ethanol 9.5 g (0.26 mol) dry hydrogen chloride are passed into 75 g ethanol over a period of 150 minutes at 15° to 20° C. Subsequently 10.56 g (0.25 mol) cyanamide is added within 15 minutes at 20° C. After 24 hours when the cyanamide has been completely converted, the solution was cooled to −10° C.; then 162.02 g (0.5 mol) of a 21% solution of sodium ethylate in ethanol is added dropwise over a period of 60 minutes also at −10° C. After adding 44.05 g (0.28 mol) malonic acid diethyl ester during 15 minutes, it is stirred for 7 days at room temperature and subsequently evaporated to dryness in a vacuum. The solution of the residue taken up in 280 g water had a pH value of 10.3. This solution was stirred into a mixture of 30 g (0.5 mol) acetic acid and 200 g water, the crystallized product is filtered, washed with 100 ml water and dried in a vacuum at 75° C.

Yield: 28.1 g=71.9%

Content (acidimetric): 99.4%

Melting point: >360° C. (it begins to decompose above 200° C.)

The representative results of the elemental analysis and of the NMR spectrum of the product from example 1 are shown here as being representative for the following examples:

Elemental analysis: In order to isolate the pure substance, the substance is re-crystallized from ethanol/water and dried over $P_2O_5$ in a vacuum desiccator.

|    | Analysis [%] | Theory [%] |
|----|--------------|------------|
| C: | 45.91        | 46.15      |
| H: | 5.10         | 5.17       |
| N: | 17.94        | 17.94      |

$^1$H-NMR spectrum ([$D_6$]DMSO):

FT-NMR spectrometer

Type: Joel-JMX-GX 400

Frequency: 100.5 MHz (C)

δ(ppm)=1.17 to 1.29 (t; 3H, J=7H$_2$, 2—C$\underline{H}_e$—CH$_2$O—); 4.25 to 4.33 (q; 2H, J=7H$_2$, 2—CH$_3$—C$\underline{H}_2$O—); 4.95 (s; 1H, —C$\underline{H}$—); 11.47 (S$_{broad}$; 2H, —O$\underline{H}$, —O$\underline{H}$);

Example 2

Starting compounds

Cyanamide and sulfuric acid in ethanol 15 kg anhydrous ethanol was added first under $N_2$ cover and cooled to −5° to −10° C. 2.5 kg (25 mol) 96% sulfuric acid was then added at −5° C. over a period of ca. 15 minutes while stirring. Subsequently a total of 1.05 kg (25 mol) cyanamide was added in portions at 0° to 10° C. and stirred in for 60 minutes. At 20° C. the after-reaction period for the complete reaction of cyanamide is about 6 hours.

After cooling the solution of O-ethylisourea hydrogen sulfate which was obtained to −10° C., 25.5 kg (75 mol) of a 20% solution of sodium ethylate in ethanol was added over a period of 60 minutes and after a further 5 minutes after-reaction 4.4 kg (27.5 mol) malonic acid diethyl ester was added dropwise within ca. 15 minutes again at −10° C. The reaction mixture was stirred for 90 hours at 25° C.; then more than ⅔ of the ethanol was removed by distillation. Subsequently water was added to dissolve the distillation residue. The pH value after dissolving the solid substance was 8.0 to 11.0.

The pH was adjusted to a final value of 4.0 at 10° to 15° C. with 3.6 kg 18% hydrochloric acid. After separating the crystallized product and washing free of sulfate using 7.5 kg water, it was dried at 75° C. in a vacuum.

Yield: 2.1 kg=57%

Content: (HPLC): 99%

Example 3

Starting compounds

Cyanamide and methanesulfonic acid in ethanol 48.5 g (0.5 mol) methanesulfonic acid was added within 5 minutes at 22° C. to 250 g ethanol while cooling slightly. 21.1 g (0.5 mol) cyanamide which had been dissolved in 100 g ethanol was added at 20° to 25° C. over a period of 30 minutes. After 17 hours stirring at room temperature, the cyanamide was completely converted. 209.35 g (0.25 mol) of the solution was cooled to −10° C. and this solution was subsequently added to 236.3 g (0.75 mol) of a 21.6% solution of sodium ethylate in ethanol within a period of 60 minutes.

After stirring for 5 minutes, 44.05 g (0.275 mol) malonic acid diethyl ester was added dropwise at −10° C. during 15 minutes. For the subsequent after-reaction, the mixture was firstly kept for 4 hours at 0° C. and subsequently for 3 days at room temperature.

The reaction mixture was evaporated in a vacuum, the residue was dissolved with 560 g water at 18° C. and the pH value was subsequently adjusted to 4.0 with 6.3 g 32% hydrochloric acid. The product which crystallizes after several minutes was filtered off, washed free of salt with 100 g water and dried in a vacuum at 80° C.

Yield: 19.75 g=50.6%

Content (acidimetric): 99.5%

Example 4

Starting compounds

Cyanamide and silicon tetrachloride 4.25 g (0.025 mol) silicon tetrachloride was stirred into 46 g (1 mol) ethanol at ca. 20° C. Afterwards 4.22 g (0.1 mol) 99.5% cyanamide was added over a period of 10 minutes at ca. 12° C. which was completely converted after 20 hours. 64.8 g (0.2 mol) of a 21% solution of sodium ethylate in ethanol was added dropwise within 10 minutes to the colourless solution cooled to −5° C. and 17.62 g (0.11 mol) malonic acid diethyl ester was added dropwise over a period of 5 minutes.

After 18 days stirring at room temperature it was concentrated by evaporation at 40° C. The colloidal components of the precipitate taken up in water were filtered off and the filtrate was adjusted to pH 4.0 with 11.6 g 32% hydrochloric acid; subsequently the product which was precipitated by acidification was separated by filtration, washed with water and dried at 75° C.

Yield: 13.2 g=84.2%

Content (acidimetric): 100%

Example 5

Starting compounds

Cyanamide and thionyl chloride 5.95 g (0.05 mol) thionyl chloride was slowly added to a solution of 4.22 g (0.1 mol) 99.5% cyanamide in 50 g ethanol while stirring and cooling. The formation of O-ethylisourea hydrochloride which proceeds exothermally was completed quantitatively after 21 hours at 21° C. After filtration, 102.7 g (0.3 mol) of a 20% solution of sodium ethylate in ethanol and 16.02 g (0.1 mol) malonic acid diethyl ester were added within 30 minutes at about 10° C. to the filtrate. Ethanol was separated by distillation at 80° C. for 90 minutes and subsequently the solid residue was dissolved in 205 ml water. The alkaline solution (pH 12.4) was adjusted to pH 4.0 with 18.4 g 32% hydrochloric acid (0.16 mol); after briefly cooling in an ice bath, the precipitate was aspirated, washed and dried at 75° C.

Yield: 8.49 g=54.4%

Content (acidimetric): 98.4%

Example 6

Starting compound

O-Ethylisourea hydrogen sulfate 490 g (2.5 mol) 95% O-ethylisourea hydrogen sulfate in 1500 g anhydrous ethanol was fed in at −10° C. and subsequently 2430 g (7.5 mol) of a 21% solution of sodium ethylate in ethanol was added dropwise over a period of 45 minutes while stirring. After 5 minutes after-reaction time, 440.5 g (2.75 mol) malonic acid diethyl ester was added dropwise within a further 15 minutes at −10° C. and the mixture was subsequently heated for 4 hours under reflux. Then about ⅔ of the alcohol was removed by distillation and replaced by the corresponding amount of water without interrupting the distillation process by this. A total of 4.2 kg aqueous-alcoholic distillate was obtained. Ca. 6 kg water was added to the mixture and it was cooled to 15° C. The product was precipitated with 196 g (1.72 mol) 32% hydrochloric acid, aspirated, washed with water and dried at 75° C.

Yield: 212 g=54%

Content ( HPLC ): 99%

Example 7

Starting compound

O-Ethylisourea hydrochloride 62.3 g (0.5 mol) O-ethylisourea hydrochloride was fed into 150 g ethanol which was present at a temperature of −5° C. Then 324 g (1.0 mol) of a 21% solution of sodium ethylate in ethanol was added dropwise over a period of 45 minutes and subsequently 88.1 g (0.5 mol) malonic acid diethyl ester was added dropwise over a period of 10 minutes. The reaction mixture was stirred for 4 hours at 0° C. and subsequently for 90 hours at room temperature. After evaporation, the residue was stirred into a solution of 30.4 g (0.5 mol) glacial acetic acid in 300 g water and the product was separated; this was washed after cooling to 17° C. (pH 6.2) and dried at 75° C. 15.2 g (0.25 mol) acetic acid was again added to the mother liquor and this was processed as described above.

Total yield: 52.8 g=68%

Content (HPLC): 95.9%

Example 8

Starting compounds

Chloroformamidinium chloride and ethanol 11.5 g (0.1 mol) chloroformamidinium chloride was added to 30 g ethanol (99%) and boiled under reflux in the absence of water. After 30 minutes the salt was dissolved and after 120 minutes the chloroformamidinium chloride was converted quantitatively into O-ethylisourea hydrochloride. After the solution had been evaporated to dryness in a vacuum, the solid white residue was dissolved in 30 g ethanol and 63 g (0.2 mol) of a 21.6% solution of sodium ethylate in ethanol was added dropwise over 15 minutes to this solution at 25° C. Subsequently 16.02 g (0.1 mol) malonic acid diethyl ester was added and the mixture was stirred for 17 hours at 25° C. After it had been boiled under reflux for a further 60 minutes and then evaporated in a vacuum, the solid residue was dissolved in 150 g water and the pH value of the solution was adjusted to 4.0 with diluted hydrochloric acid. The crystalline precipitated product was aspirated, washed free of salt with water and dried at 75° C. in a vacuum.

Yield: 6.4 g=42.7%

Content (acidimetric): 99.5%

Example 9

Starting compounds

Chloroformamidinium chloride and cyanamide in ethanol 11.5 g (0.1 mol) chloroformamidinium chloride was stirred at 25° C. together with 30 g ethanol (99%) and 4.2 g (0.1 mol) cyanamide in the absence of water. The components were present in the dissolved form after 120 minutes and had been converted quantitatively into O-ethylisourea hydrochloride after a total of 20 hours. Subsequently the solution was concentrated by evaporation in a vacuum and 12.4 g (0.1 mol) of the solid salt was again dissolved in ethanol. 63 g (0.2 mol) of a 21.6% solution of sodium ethylate in ethanol was added dropwise at 0° C. over a period of 15 minutes while cooling in an ice bath, then 16.02 g (0.1 mol) malonic acid diethyl ester was added and the reaction mixture was stirred for 18 hours at 25° C. After boiling for 1 hour under reflux, it was concentrated by evaporation in a vacuum, the residue was subsequently dissolved in 150 g water and the pH value was adjusted to 3.0 to 4.0 with dilute hydrochloric acid. The crystalline precipitate was filtered off, the product was washed free of chloride with water and dried at 75° C. in a vacuum.

Yield: 6.4 g=41.0%

Content (acidimetric): 98.7%

Example 10

Starting compounds

Chloroformamidinium chloride and cyanamide in ethanol

A solution of 0.25 mol O-ethylisourea hydrochloride in ethanol was prepared from chloroformamidinium chloride and cyanamide according to example 9 and subsequently admixed at 10° C. with 0.5 mol of a 21% sodium methylate solution in ethanol. The reaction mixture obtained in this way was added dropwise to 140 g (0.87 mol) malonic acid diethyl ester at 130° to 145° C. over a period of 3 hours while stirring and the ethanol was removed by distillation in a gentle stream of nitrogen. After cooling to 15° C., the solid residue consisting of sodium 2-ethoxy-4,6-dihydroxypyrimidine and sodium chloride was aspirated, washed with ethanol and subsequently processed according to example 9.

Yield: 28.1 g=72.0%

Content (HPLC): 99.3%

Example 11

Starting compounds

O-Ethylisourea hydrogen sulfate in methanol and sodium methylate 270 g (1.5 mol) of a 30% solution of sodium methylate in methanol was added dropwise at −1° to −7° C. over a period of 75 minutes to 98 g (0.5 mol) O-ethylisourea hydrogen sulfate in 300 g anhydrous methanol. Then 66.1 g (0.5 mol) malonic acid dimethyl ester was added at −5° C. within 30 minutes and the reaction mixture was stirred for 3 hours at 0° C. and subsequently for 5 days at 25° C. After mild evaporation at 30° to 40° C. in a vacuum, 188.6 g of a white-yellow residue was obtained which was converted into a yellow solution with 1490 g water (pH: 10.0). A white precipitate was precipitated with 54.2 g (0.475 mol) of 32% hydrochloric acid, filtered off, washed with 250 g water and the product was dried at 80° C. in a vacuum.

Yield: 54.3 g=69.5%

Content (HPLC): 91.4% 2-ethoxy-4,6-dihydroxypyrimidine 8.4% 2-methoxy-4,6-dihydroxypyrimidine The NMR spectrum of this product has a peak at 3.82 ppm (—O$\underline{C}$H$_3$) in addition to the known peaks (cf. example 1).

Example 12

Starting compounds

O-Ethylisourea and sodium ethylate (mole ratio 1:1)

18.6 g (0.2 mol) O-ethylisourea (content: 94.8%) was added at 20° C. to 32.04 g (0.2 mol) malonic acid diethyl ester within 3 minutes. Subsequently 65.7 g (0.2 mol) of a 20.7% solution of sodium ethylate in ethanol was added dropwise over a period of 35 minutes at 12° to 25° C., the reaction mixture was stirred for 70 hours at 20° C. and then concentrated by evaporation at 50° C. in a vacuum. 40.4 g of a yellow solid substance was obtained which was dissolved in 400 g water. The solution was cooled to 10° to 15° C. and the pH value was adjusted from 11.0 to 4.0 by addition of 24.2 g (0.21 mol) of 32% hydrochloric acid. After stirring for 30 minutes in an ice bath, it was filtered off, the product was washed with water and dried at 75° C. in a vacuum.

Yield: 18.61 g=59.6%

Content (acidimetric): 98.0%

(HPLC): 97.5%

Example 13

Starting compound

O-Ethylisourea (mole ratio base: ester=2:1)

18.6 g (0.2 mol) of 94.8% O-ethylisourea base was stirred for 70 hours at room temperature into 16.02 g (0.1 mol) malonic acid diethyl ester. The almost solid mass was subsequently freed of formed ethanol at 50° C. in a vacuum. The 45 g of the residue of fatty consistency was dissolved in 500 g water and the pH value was subsequently adjusted to 3.4 with 4.1 g concentrated sulfuric acid. After stirring for 15 minutes in an ice bath, it was filtered off, the product was washed with water and dried at 75° C. in a vacuum.

Yield: 5.06 g=32.4%

Content (acidimetric): 97.4%

Example 14

Starting compounds

O-Ethylisourea hydrogen sulfate sodium salt of malonic acid diethyl ester 3400 g anhydrous ethanol and 1367 g (7.5 mol) sodium malonic acid diethyl ester were added first. Subsequently at −5° to 0° C. 466 g (2.5 mol) pure O-ethylisourea hydrogen sulfate was fed into this in portions while stirring vigorously. Subsequently it was heated for 24 hours under reflux. The reaction mixture was then processed according to example 6.

Yield: 285 g=73%

Content (HPLC): 99.2%

Example 15

Starting compound

O-Ethylisourea hydrochloride in ethanolic solution

A solution of 0.5 mol O-ethylisourea hydrochloride was prepared according to example 1 in 150 g ethanol (absolute). Subsequently 1 mole of a 21% ethanolic sodium ethylate solution was added at 0° C. while stirring. The precipitated sodium chloride was filtered off while excluding atmospheric humidity and 88.5 g (0.55 mol) malonic acid diethyl ester was added to the filtrate at 20° C. over a period of 1 hour. The reaction mixture was subsequently heated for 25 hours under reflux and afterwards concentrated by evaporation on a rotary evaporator until a suspension was present which can just be stirred and pumped. The precipitate was aspirated, washed with ethanol and dried at 90° C. in a vacuum of a water-jet pump.

Yield: 69 g sodium salt of 2-ethoxy-4,6-dihydroxy-pyrimidine=77.5%

Melting point: >360° C.

Content (HPLC): 99%

We claim:

1. Process for the production of 2-ethoxy-4,6-dihydroxypyrimidine, its tautomers or its alkali salts, wherein O-ethylisourea or a salt thereof is reacted with a malonic acid dialkyl ester and an alcoholate or a salt of the malonic acid dialkyl ester in the presence of a solvent at −10° to 180° C. and, if desired, the alkali salt of the 2-ethoxy-4,6-dihydroxypyrimidine obtained is converted into the free pyrimidine derivative by acidification with a mineral acid or a carboxylic acid.

2. Process as claimed in claim 1, wherein
   the O-ethylisourea salt or ethylisourea are produced from cyanamide or chloroformamidinium salts.

3. Process as claimed in claim 1, wherein
   the O-ethylisourea salt or O-ethylisourea are produced in situ and reacted without further purification.

4. Process as claimed in claim 1, wherein an alkali alcoholate is used as the alcoholate.

5. Process as claimed in claim 1, wherein the O-ethylisourea salt is produced by reacting cyanamide with ethanol in the presence of a mineral acid, anhydrous hydrogen chloride or a strong organic acid.

6. Process as claimed in claim 5, wherein concentrated sulfuric acid or a mixture of technical grade sulfuric acid and fuming sulfuric acid is used as the mineral acid.

7. Process as claimed in claim 5, wherein
   a sulfonic acid or a haloacetic acid is used as the strong organic acid.

8. Process as claimed in claim 7, wherein
   methanesulfonic acid, benzenesulfonic acid, p-toluenesulfonic acid or trichloroacetic acid is used.

9. Process as claimed in claim 1, wherein the O-ethylisourea salt is produced by reacting cyanamide with ethanol in the presence of a compound that cleaves off HCl.

10. Process as claimed in claim 9, wherein
    silicon tetrachloride or thionyl chloride is used as the compound that cleaves off HCl.

11. Process as claimed in claim 1, wherein the O-ethylisourea salt is produced by reacting chloroformamidinium chloride with ethanol.

12. Process as claimed in claim 1, wherein the O-ethylisourea salt is produced by reacting chloroformamidinium chloride with ethanol in the presence of cyanamide.

13. Process as claimed in claim 1, wherein the O-ethylisourea salt is produced at temperatures between −10° and +90° C.

14. Process as claimed in claim 1, wherein the mole ratio of isourea or its salt to the alcoholate or to the salt of the malonic acid dialkyl ester is 1:1 to 8.

15. Process as claimed in claim 1, wherein sodium ethylate is used as the alcoholate.

16. Process as claimed in claim 1, wherein the reaction of O-ethylurea or its salt is carried out in the temperature range of 70° to 140° C.

17. Process as claimed in claim 1, wherein an O-ethylisourea salt is reacted with an alkali malonic acid dialkyl ester.

18. Process as claimed in claim 1, wherein ethanol or an excess of malonic acid dialkyl ester is used as the solvent.

19. Process as claimed in claim 1, wherein malonic acid diethyl ester is used as the malonic acid dialkyl ester.

20. Process as claimed in claim 1, wherein after the reaction of the O-ethylurea or its salts the solvent is at least partially removed.

21. Process as claimed in claim 20, wherein
    the solvent is removed by distillation.

22. Process as claimed in claim 1, wherein the reaction product is taken up in an aqueous phase and acidified to a pH value between 2.0 and 9.0.

23. Process as claimed in claim 22, wherein
    it is acidified to a pH value of 3.5 to 5.5.

24. Process as claimed in claim 23, wherein
    a mineral or carboxylic acid is used for the acidification.

25. Process as claimed in claim 24, wherein
    hydrochloric acid, sulfuric acid or acetic acid is used.

26. Process as claimed in claim 22, wherein in a subsequent processing step the product in the form of a solid substance is washed salt-free with water and, if desired, dried.

27. Process as claimed in claim 1, wherein sodium alcoholate is used as the alcoholate.

28. Process as claimed in claim 17, wherein said alkali malonic acid dialkyl ester is a sodium malonic acid dialkyl ester.

* * * * *